United States Patent

Nagasawa

Patent Number: 6,076,959
Date of Patent: Jun. 20, 2000

[54] TOTAL-INTERNAL-REFLECTION TYPE DEPOSIT POINT SENSOR

[75] Inventor: Yasushi Nagasawa, Urawa, Japan

[73] Assignee: Japan Energy Corporation, Tokyo, Japan

[21] Appl. No.: 09/029,772

[22] PCT Filed: Jul. 2, 1997

[86] PCT No.: PCT/JP97/02280

§ 371 Date: Mar. 3, 1998

§ 102(e) Date: Mar. 3, 1998

[87] PCT Pub. No.: WO98/01748

PCT Pub. Date: Jan. 15, 1998

[30] Foreign Application Priority Data

Jul. 3, 1996 [JP] Japan .................................. 8-192813

[51] Int. Cl.[7] .......................... G01N 25/04; G01N 21/43
[52] U.S. Cl. ............................... 374/20; 374/18; 374/19; 356/136
[58] Field of Search ................................ 374/18, 19, 20, 374/17, 16; 356/128–137

[56] References Cited

U.S. PATENT DOCUMENTS

| | | | |
|---|---|---|---|
| 5,088,833 | 2/1992 | Tsang et al. | 374/20 |
| 5,565,978 | 10/1996 | Okubo et al. | 356/128 |
| 5,641,230 | 6/1997 | Okubo | 374/20 |

FOREIGN PATENT DOCUMENTS

| | | |
|---|---|---|
| 61-17941A | 1/1986 | Japan . |
| 80 68753A | 3/1996 | Japan . |
| 8-240544A | 9/1996 | Japan . |
| 9424544A1 | 10/1994 | WIPO . |

*Primary Examiner*—Diego Gutierrez
*Assistant Examiner*—Stanley J. Pruchnic, Jr.
*Attorney, Agent, or Firm*—Birch, Stewart, Kolasch & Birch, LLP

[57] ABSTRACT

A novel method for measuring a deposit point is provided, which makes it possible to quickly and accurately measure a cloud point. A test sample is irradiated at an angle of incidence $\theta$ with an incoming light beam which satisfies an expression $\theta<\theta_2$ while gradually cooling the test sample such as gas oil, and a totally reflected light beam from the test sample is detected for every temperature, provided that $\theta_2$ represents a critical angle of total reflection of a deposit such as a paraffin component deposited when the test sample is cooled. The deposit point of the test sample is determined from a change in intensity of the totally reflected light beam with respect to the change in temperature. The light intensity distributions, detected by a sensor array at respective temperatures, are statistically processed to more accurately determine the deposit point. A total reflection type sensor, having a waveguide structure formed with a light-incoming optical path and a light-emitting optical path, is used in determining the deposit point. CCD is used as a detector.

18 Claims, 13 Drawing Sheets

IN CASE OF $\theta < \theta_1$ (TRANSMITTED THROUGH BOTH SAMPLE AND DEPOSIT)

IN CASE OF $\theta > \theta_2$ (TOTALLY REFLECTED BY BOTH SAMPLE AND DEPOSIT)

IN CASE OF $\theta_1 < \theta < \theta_2$ (TOTALLY REFLECTED BY SAMPLE, AND TRANSMITTED THROUGH DEPOSIT)

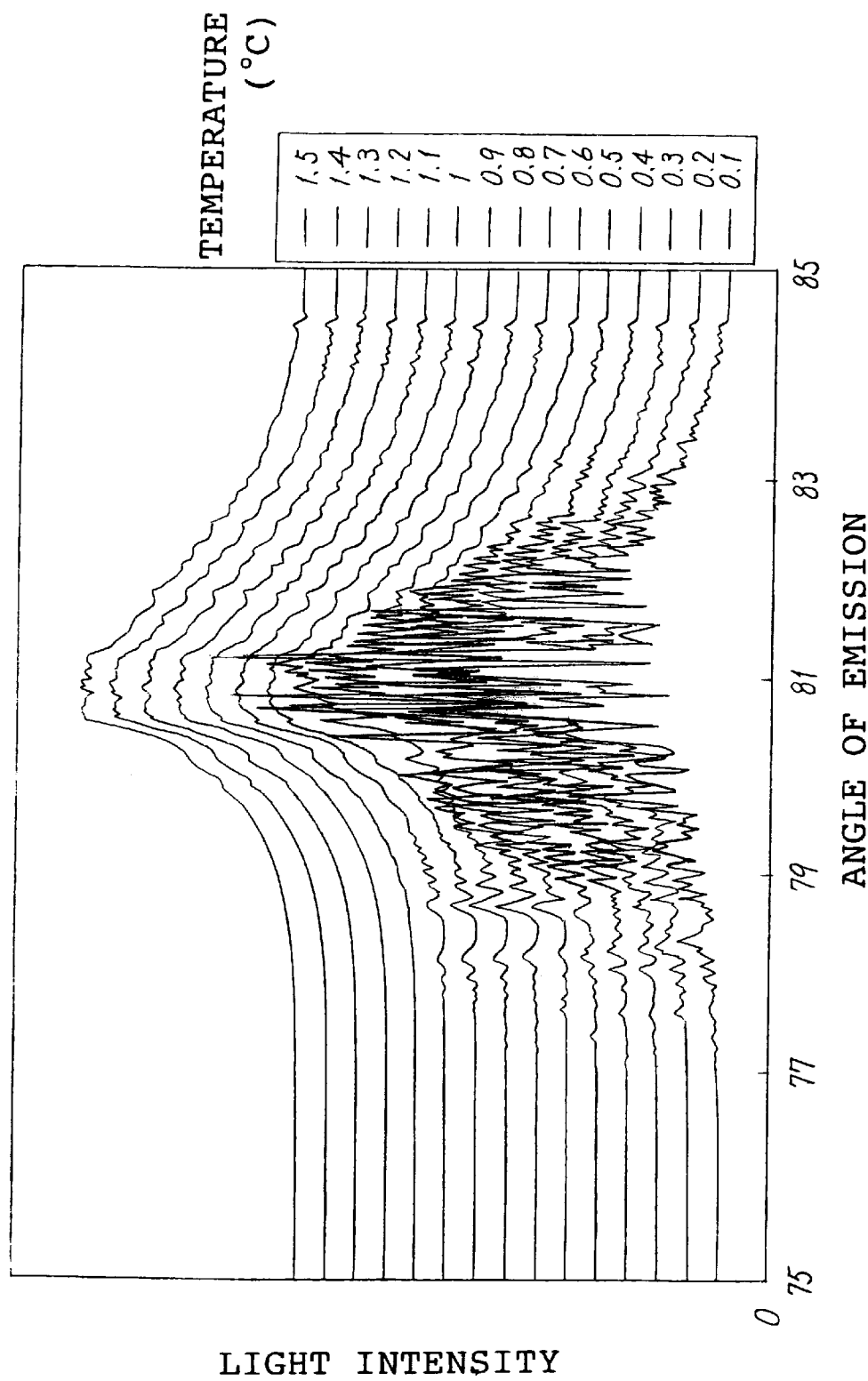

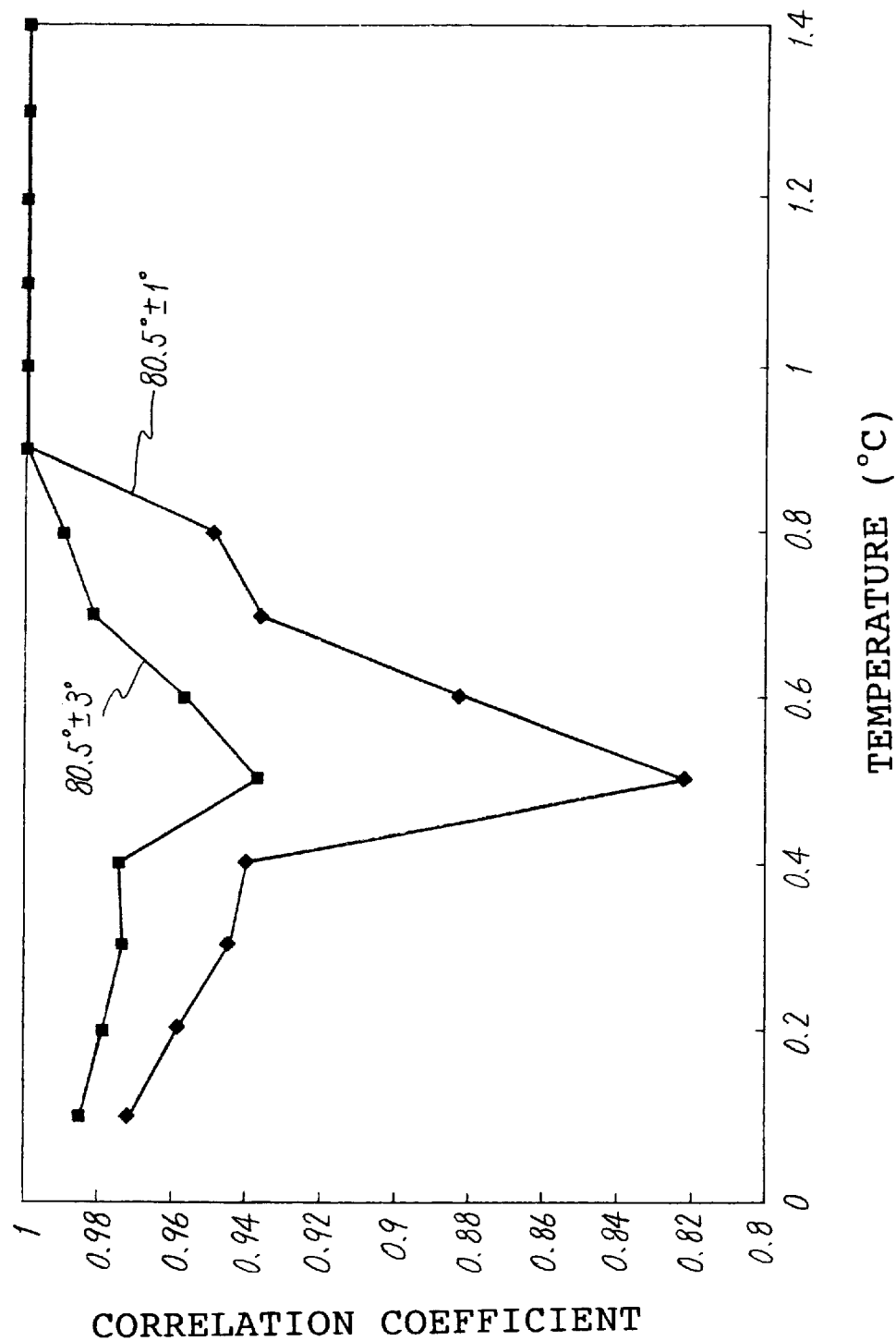

TOTAL-INTERNAL-REFLECTION TYPE DEPOSIT POINT SENSOR

This application claims the benefit under 35 U.S.C. §371 of prior PCT International Application No. PCT/JP97/02280 which has an International filing date of Jul. 2, 1997 which designated the United States of America, the entire contents of which are hereby incorporated by references.

TECHNICAL FIELD

The present invention relates to a method for measuring a deposit point and a deposit point meter. In particular, the present invention relates to a method for measuring a deposit point and a deposit point meter which make it possible to quickly and highly accurately measure the deposit point by using a small amount of a sample. Especially, the present invention relates to a method for measuring a deposit point and a deposit point meter which make it possible to quickly and highly accurately measure the cloud point of a petroleum product.

BACKGROUND ART

The cloud point meter is a measuring instrument for measuring the temperature at which a petroleum product begins to cloud as a result of deposition of paraffin wax contained in the petroleum product when the petroleum product such as gas oil is cooled under a predetermined condition. The phenomenon of deposition of solid matters is not limited to the petroleum product, which is also observed in the same manner at a relatively low temperature for many chemical products such as plasticizers and surface active agents. Therefore, in order to evaluate the quality of these products, it is extremely important to accurately measure the cloud point.

Japanese Industrial Standard (JIS) K 2269 specifies the method for testing the pour point of crude oil and petroleum products and the cloud point of petroleum products. According to the test method as described above, a certain amount of a sample is prepared, and it is maintained at a temperature higher than an expected cloud point by not less than 14° C. The sample is placed in an outer tube of a cooling bath so that the sample is allowed to arrive at a temperature in the vicinity of the expected cloud point. After that, the sample is taken out every time when the temperature of the sample is lowered by 1° C. to investigate whether or not any cloud appears at the bottom portion of the sample. This operation is laborious, and it takes a long time to perform the measurement. For this reason, it is approved to use an automatic cloud point meter on condition that a result obtained by using the automatic cloud point meter can be confirmed to be not significantly different from a result obtained by using the specified test method, in accordance with JIS Z 8402.

For example, Japanese Laid-Open Patent Publication No. 61-17941 discloses a cloud point meter having a structure comprising a sample vessel for pouring a liquid sample thereinto and a pair of optical fibers connected to a light-projecting unit and a light-receiving unit, the pair of optical fibers being installed in the sample vessel, wherein a projecting light beam outgoing from one of the optical fibers and passing through the sample is reflected by a mirror surface disposed at the bottom surface of the vessel, and a reflected light beam is received by the other optical fiber. In this apparatus, any cloud is allowed to appear at the bottom surface of the vessel by cooling the sample. The cloud point of the sample is determined by observing rapid change in amount of received light coming from the bottom surface.

The present applicant has disclosed an automatic apparatus for measuring the cloud point in International Publication No. WO 94/24544. This apparatus has a sensor including, on a substrate, a laminate of a waveguide assembly comprising a light-introducing optical path and a light-emitting optical path which intersect with each other at a detecting surface to make contact with a test liquid, and a means for heating and cooling the test liquid. The angle of incidence and the angle of reflection of light with respect to the test sample are adjusted to give angles at which total reflection is caused by a deposit such as paraffin generated in the sample, at the detecting surface for the light-introducing optical path and the light-emitting optical path. When the test liquid is gradually cooled, the incoming light beam is refracted at the detecting surface to go toward the test liquid before arrival at the cloud point of paraffin. However, upon arrival at the cloud point, total reflection occurs at the detecting surface as a result of deposition of a solid matter of paraffin. The totally reflected light beam is detected by the aid of an optical fiber connected to the light-emitting optical path. Namely, this apparatus detects the deposition of a solid matter on the basis of the on/off system for the totally reflected light beam coming from the solid matter, wherein the temperature upon the detection is read to determine the cloud point.

The present applicant has also disclosed, in Japanese Patent Application No. 07-068979, a cloud point meter having approximately the same arrangement as that of the cloud point meter disclosed in International Publication No. WO 94/24544. The cloud point meter comprises a concave detecting area formed by an area including a point of intersection between a light-introducing optical path and a light-emitting optical path of a waveguide path, of a contact surface with respect to a test liquid. This cloud point meter is operated as follows. Namely, when deposited fine particles are generated in the detecting area as a result of cooling for the sample, the incoming light beam is optically scattered by the fine particles. The light beam is introduced into the light-emitting optical path, and it is detected by an optical fiber for the outgoing light beam. This cloud point meter makes it possible to quickly and accurately measure the cloud point by sensing and detecting the appearance of initially formed fine particles.

The cloud point meter concerning the conventional technique as described above greatly shortens the time required for measurement, as compared with the measuring method specified in JIS K 2269. However, it is demanded to provide a cloud point meter which makes it possible to more quickly and more accurately measure the cloud point.

An object of the present invention is to provide a novel method for measuring the deposit point (deposition point), which makes it possible to quickly and accurately measure the deposit point such as the cloud point. Another object of the present invention is to provide a deposit point meter which makes it possible to quickly and accurately measure the deposit point, and which can be easily produced.

DISCLOSURE OF THE INVENTION

According to a first aspect of the present invention, there is provided a method for measuring a deposit point, comprising the steps of irradiating a test sample, for which the deposit point is measured, with a light beam from the outside and detecting a reflected light beam coming from a contact surface between the test sample and the outside, while changing a temperature of the test sample, characterized by: irradiating the test sample with the incoming light beam at an angle of incidence θ which satisfies an expression $(\theta_1-\Delta)<\theta<(\theta_2+\Delta)$ while changing the temperature of the test sample, wherein the incoming light beam is a light beam having a spreading angle $\pm\Delta$, $\theta_1$ represents a critical angle of total reflection of the test sample, and $\theta_2$ represents a critical angle of total reflection of a deposit deposited when the test sample is cooled; detecting a totally reflected light beam from the test sample; and determining the deposit point of the test sample from change in intensity of the totally reflected light beam with respect to the change in temperature.

In the case of the cloud point meter described in International Publication No. WO 94/24544, the cloud point has been measured by detecting a light beam totally reflected by paraffin when a test liquid is cooled, and paraffin in the test liquid is deposited. On the contrary, in the case of the method for measuring the deposit point according to the present invention, the deposit point is measured on the basis of the principle as shown in FIG. 1. FIG. 1 conceptually shows the situation in which the incoming light beam is refracted or totally reflected at a detecting surface 16 of a sensor when the light beam is radiated from a core portion 12 (refractive index: $n_0$) of a waveguide layer of the sensor toward a test liquid 14 (refractive index: $n_1$). The angle of incidence (critical angle) $\theta_1$, at which the incoming light beam is totally reflected at the detecting surface, is determined by $\sin\theta_1=n_1/n_0$ according to the Snell's law. On the other hand, assuming that a solid matter 18 such as paraffin, which is deposited from the test liquid when the test liquid is cooled, has a refractive index $n_2$, the critical angle of total reflection $\theta_2$, at which the incoming light beam coming from the core 12 of the waveguide layer is totally reflected by the deposit 18, is determined by $\sin\theta_2=n_2/n_0$. For example, when the cloud point of a petroleum product is measured, if the test liquid is the petroleum product such as gas oil, and the deposit is the paraffin component, then an expression of $\theta_1<\theta_2$ is generally satisfied. FIG. 1A shows a case in which the angle of incidence is $\theta<\theta_1$. Before the paraffin component is deposited (before cooling is performed), all of the incoming light beam is refracted at the detecting surface, and it is transmitted through the test liquid 14 as shown in the left part of FIG. 1A. Even when the test liquid is cooled to deposit the solid matter 18 such as paraffin on the detecting surface 16 from the test sample 14 as shown in the right part of FIG. 1A, no total reflection occurs from the deposit 18 in conformity with the total reflection condition as described above, and the incoming light beam is transmitted through the detecting surface 16. It is noted that no spreading angle $\pm\Delta$ is taken into account for the incoming light beam shown in FIG. 1.

When the angle of incidence θ satisfies $\theta_2<\theta$, the incoming light beam is totally reflected by the test liquid 14 before cooling as shown in FIG. 1B in conformity with the total reflection condition. The incoming light beam is also totally reflected by the deposit 18 deposited by cooling.

On the other hand, when the angle of incidence θ satisfies $\theta_1<\theta<\theta_2$, the incoming light beam is totally reflected by the test sample 14 as shown in FIG. 1C. However, the incoming light beam is not totally reflected by the deposit 18 deposited as a result of cooling. Accordingly, when the test sample is gradually cooled to arrive at the deposit point (cloud point) for the paraffin component or the like, then the deposit 18 is deposited at the detecting surface 16, and the intensity of reflected light from the detecting surface 16 is lowered. Therefore, it is understood that the cloud point can be determined by setting the angle of incidence θ to be within the range of $\theta_1<\theta<\theta_2$, and observing the change in intensity of reflected light with respect to the cooling temperature. Especially, the deposited solid matter of the paraffin component forms polycrystals which grow from crystal nuclei. Therefore, a minute amount of the crystals appear in a form of lands on the detecting surface at the initial stage of deposition. The method of the present invention makes it possible to perform detection at the initial stage of crystal deposition as described above. Therefore, it is possible to determine the cloud point extremely accurately. As illustrated in embodiments described later on, the condition is not limited to only $\theta_1<\theta<\theta_2$, because the angle of incidence θ has a spreading angle. Namely, the reflected light beam may be sampled within an angle range in which θ is smaller than $\theta_1$, for example, in an angle range in which the angle of incidence θ satisfies $(\theta_1-\Delta)<\theta<(\theta_2+\Delta)$ provided that the incoming light beam is represented as having an angle $\alpha\pm\Delta$ based on a central angle α as a reference.

In the method for measuring the deposit point according to the present invention, a correlation coefficient between light intensity distributions of detected totally reflected light beams may be determined as a function of temperature, and the deposit point may be determined according to temperature-dependent change in the correlation coefficient. The deposit point can be determined more accurately by statistically processing the intensity of the totally reflected light as described above. Especially, it is possible to accurately determine the cloud point of petroleum products.

According to a second aspect of the present invention, there is provided a deposit point meter comprising a sensor including a waveguide layer formed with a light-introducing optical path for introducing a light beam into a contact surface with respect to a test sample for which a deposit point is measured and a light-emitting optical path for emitting a reflected light beam coming from the contact surface, a light-supplying means connected to the waveguide layer for supplying the light beam to the light-introducing optical path, and a photodetector connected to the waveguide layer for detecting the light beam coming from the light-emitting optical path; and a heating and cooling means for controlling a temperature of the test sample; wherein the light-introducing optical path and the light-emitting optical path are formed in the waveguide layer so as to detect a light beam having an angle of incidence θ which satisfies an expression $(\theta_1-\Delta)<\theta<(\theta_2+\Delta)$ provided that the incoming light beam is a light beam having a spreading angle $\pm\Delta$, $\theta_1$ represents a critical angle of total reflection of the test sample, and $\theta_2$ represents a critical angle of total reflection of a deposit deposited when the test sample is cooled. The light intensity at a certain temperature can be sensed and detected more sensitively by appropriately selecting the range of the angle of reflection to be detected within the scope of the condition specified by the present invention.

In the deposit point meter according to the present invention, it is preferable that the sensor comprises a laminate having a clad/core/clad-configured waveguide structure on a substrate, an optical fiber for supplying the light beam to the light-introducing optical path, and a photoelectric sensor array for detecting the light beam coming from the light-emitting optical path, wherein the laminate comprises a light-introducing surface connected to the optical fiber, a detecting surface for totally reflecting or transmitting the incoming light beam having the spreading angle radiated from the optical fiber and defining a contact surface with respect to the test sample, and a light-emitting surface connected to the photoelectric sensor array.

In the deposit point meter according to the present invention, it is preferable that the test sample is cooled on a side of the detecting surface of the sensor, because it is possible to accurately sense and detect the deposition temperature of a solid matter. It is advantageous that the core layer of the sensor has a thickness which is not larger than a size of particles deposited when the test sample is cooled, in order to perform high sensitivity detection. It is preferable that the thickness of the core layer is not more than 1 mm. It is necessary that the thickness of the core layer is not less than 1 μm, in order to achieve waveguide for the light beam introduced into the core layer with little loss of light.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 1 illustrates the principle of the method for measuring the deposit point according to the present invention, wherein FIG. 1C shows a case in which the angle of incidence θ satisfies θ$_1$<θ<θ$_2$, and wherein FIGS. 1A to 1C shows situations of refraction or reflection of the introduced light beam before or after the cooling for the test sample respectively.

FIG. 4 conceptually shows magnified cross sections in the vicinity of the core layer 3 of the waveguide layer shown in FIG. 1 and relationships with respect to deposited particles 41, wherein

FIG. 5 shows a graph illustrating relationships between the angle of emission and the light intensity detected by a CCD sensor, obtained when No. 2 gas oil is cooled from a temperature of 1.5° C. at a cooling speed of 0.1° C./second.

FIG. 6 shows a graph illustrating relationships between the correlation coefficient and the temperature obtained from the result shown in FIG. 5, depicting two cases based on the use of detection data from the sensor array corresponding to a critical angle of total reflection of 80.5°±3° and a critical angle of total reflection of 80.5°±1° of No. 2 gas oil respectively.

BEST MODE FOR CARRYING OUT THE INVENTION

Structure of deposit point meter

Figure 2:
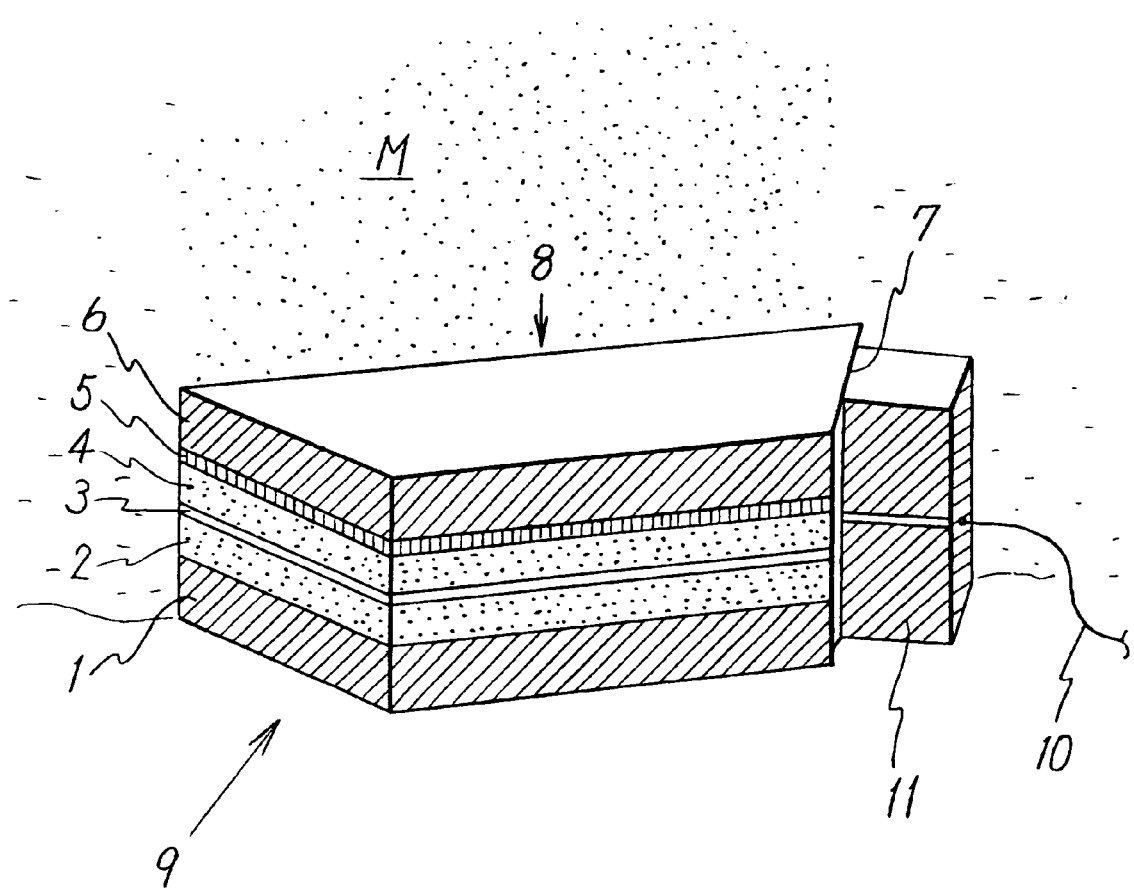
FIG. 2 shows a perspective view of main parts of a specified embodiment of a total reflection type optical sensor used for the deposit point meter as illustrated in applicant's previous U.S. Pat. No. 5,565,978.

Embodiments and examples of the present invention will be explained with reference to the drawings. FIG. 2 shows a perspective view of main parts of a specified embodiment of a total reflection type optical sensor used for the deposit point meter according to the present invention. The total reflection type sensor has a structure constructed by successively laminating a clad glass plate, a core glass plate, and a clad glass plate on a substrate 1 so that a waveguide structure of clad 2/core 3/clad 4 is formed on the substrate 1, and sticking a substrate 6 on the clad 4 via an adhesive 5. The lower substrate 1 and the upper substrate 6 may be composed of, for example, Si substrates and metal substrates. Those usable as materials for the core 3 and the clads 2, 4 include materials which are generally used as materials for optical fibers. For example, the core/clad material may be $SiO_2/SiO_2+GeO_2$, $SiO_2/SiO_2+TiO_2$, $SiO_2+SiF_4/SiO_2$. The clads 2, 4 and the core 3 can be formed on the lower substrate 1 in accordance with the conventional film formation technique such as sputtering. For example, an epoxy resin is used as the adhesive 5.

The clad/core/clad-configured waveguide structure may be constructed by using an assembly in which the core is formed by a waveguide glass plate having a thickness of 0.2 mm to 1 mm which is interposed and glued between materials for forming the clads. The assembly is further interposed between substrates, if necessary. Those usable as the waveguide glass plate to be used as the core include glass such as quartz glass and optical glass, and optical crystals such as sapphire, zirconia, and diamond. Those usable as the material for the clad include glass such as quartz glass and optical glass, and optical crystals such as sapphire, zirconia, and diamond, each having a refractive index lower than that of the waveguide glass plate to be used for the core. Those usable as the substrate include, for example, Si and metals having high heat-conductivity. Those usable as the adhesive to glue the core and the clads include, for example, epoxy resins for optical purpose. Those usable as the adhesive to glue the substrate and the clads include, for example, epoxy resins.

The laminate comprises a light-introducing surface 7 for introducing the light beam into the waveguide layer formed by the clad 2/core 3/clad 4, a detecting surface 8 for reflecting or transmitting the incoming light beam and constructing the contact surface with respect to a test sample M, and a light-emitting surface 9 for outputting the reflected light beam. The light-introducing surface 7 is connected to an optical fiber array 11 in which, for example, a single mode optical fiber 10 is embedded. The optical fiber is connected to a light source (not shown) such as a semiconductor laser composed of, for example, GaAs—AlGaAs, a He—Ne laser, or a light emitting diode (LED). A CCD sensor (see FIG. 3), which serves as a photodetector capable of detecting, in a wide range, the reflected light beam obtained from the incoming light beam having a spreading angle, is connected to the light-emitting surface 9. Preferably, the photodetector is installed with a computing unit (see FIG. 3) for statistically processing the intensity of received light obtained by each of pixels of the CCD sensor.

Figure 1A:
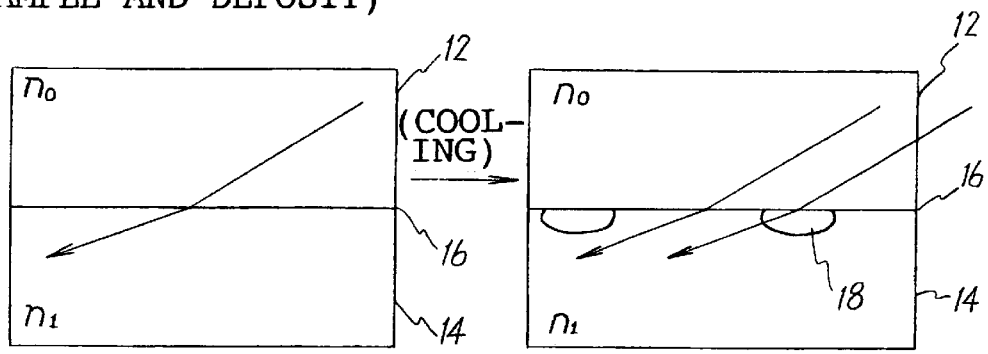
FIG. 1A shows a case in which the angle of incidence θ satisfies θ<θ$_1$.
Figure 1B:
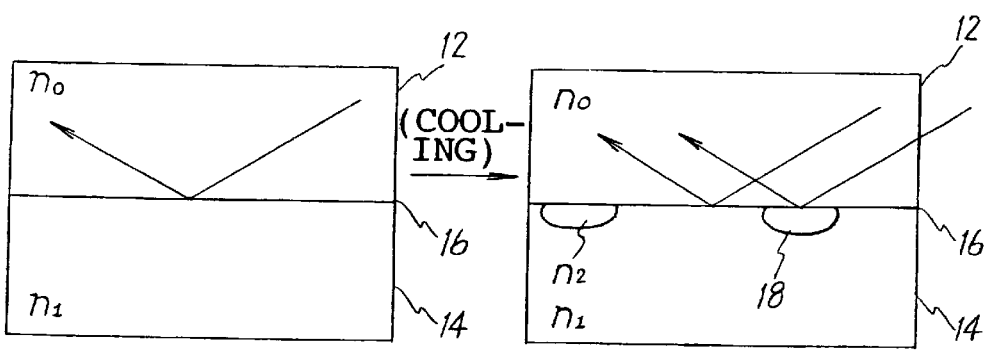
FIG. 1B shows a case in which the angle of incidence θ satisfies θ$_2$<θ.
Figure 1C:
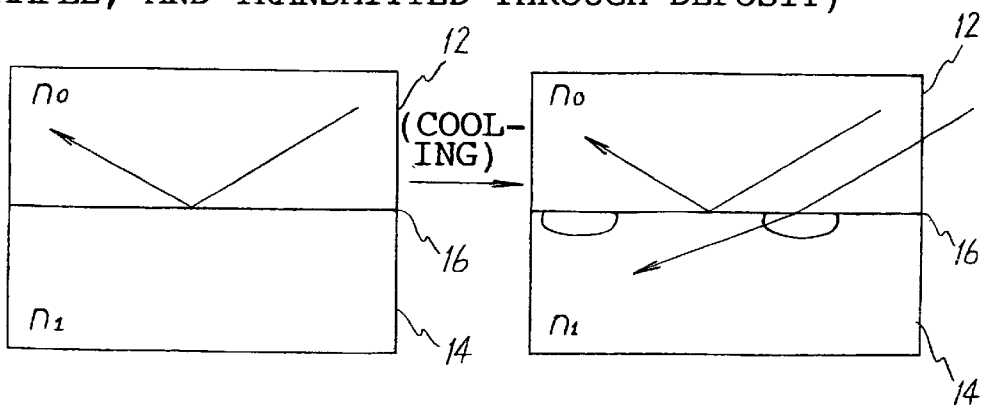
Figure 3:
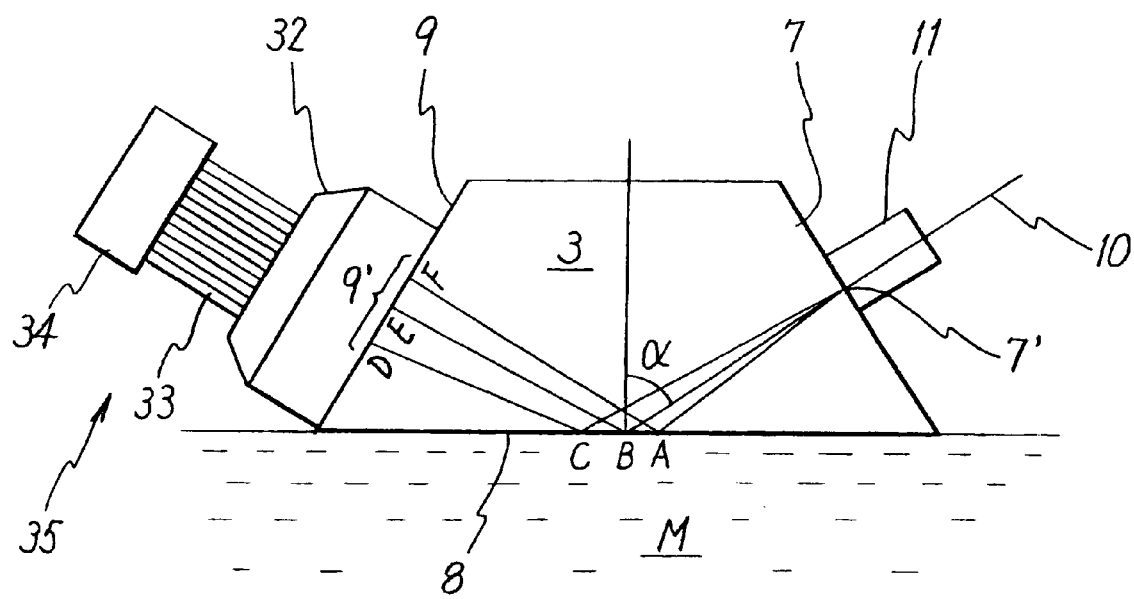
FIG. 3 illustrates a detection system and a principle of operation of the sensor shown in FIG. 2, depicting a cross-sectional structure of the sensor including the core layer shown in FIG. 2.

FIG. 3 illustrates a detection system and a principle of operation of the sensor shown in FIG. 2. FIG. 3 shows a cross-sectional structure of the sensor including the core 3 of the waveguide layer shown in FIG. 2. The light beam coming from the fiber 10 is introduced through the optical fiber array 11 into a light-introducing position 7' on the light-introducing surface 7. The outgoing light beam emitted from the optical fiber is spread at a spreading angle $\pm\Delta$, usually at an angle of about 6 to 8 degrees. Then the light beam passes through the waveguide layer (light-introducing optical path) therefrom while maintaining the spreading angle $\pm\Delta$, and it arrives at the detecting surface 8 which contacts with the test sample M, while giving a central angle of incidence $\alpha$ with the spreading angle ($\alpha\pm\Delta$). The center of the arrival point is indicated by B, and the both ends are indicated by A and C. The angle of incidence is ($\alpha-\Delta$) at Point A, and it is ($\alpha+\Delta$) at Point C. Assuming that the light beam is totally reflected by the boundary plane between the detecting surface 8 and the test sample M, reflected light beams from Points A, B, C arrive at Points D, E, F at the light-emitting position 9' on the light-emitting surface 9 respectively. The CCD sensor 32 detects outgoing light beams ranging over Points D, E, F. For the CCD sensor 32, it is possible to use a linear array CCD sensor comprising a plurality of pixels arranged linearly in a direction from D to F (for example, the sensor has 1024 pixels in the direction from D to F (14 $\mu$m/pixel)). In order to process the change in light intensity of the outgoing light beam, the output from the CCD sensor 32 is sent via signal lines 33 to a computing unit 34. The computing unit 34 performs statistical processing as described later on. A photodetector 35 is constructed by the CCD sensor 32, the signal lines 33, and the computing unit 34. The total reflection type optical sensor has the structure equivalent to that of a reflection type refractive index sensor disclosed by the present applicant in FIGS. 1 and 2 in International Publication No. WO 94/24544 and in U.S. Pat. No. 5,565,978, issued Oct. 15, 1996.

As shown in FIG. 3, the incoming light beam has the spreading angle $\alpha\pm\Delta$, and the reflected light beams corresponding thereto are detected by the CCD sensor 32. Therefore, the angle of reflection, at which total reflection from the test sample occurs, can be detected as a boundary between light and darkness by using the CCD sensor 32. The relationship between the refractive index of the test sample and the pixel position of the CCD sensor 32 indicating the critical angle of total reflection can be determined beforehand by previously measuring the boundary between light and darkness by using several test samples having different refractive indexes.

Figure 4A:
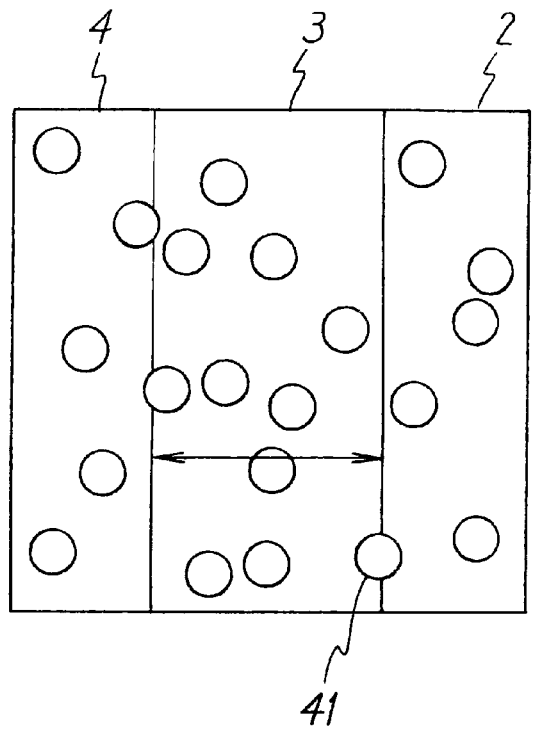
FIG. 4A shows a case in which the thickness of the core layer is sufficiently thicker than the particle size of the deposited particles.
Figure 4B:
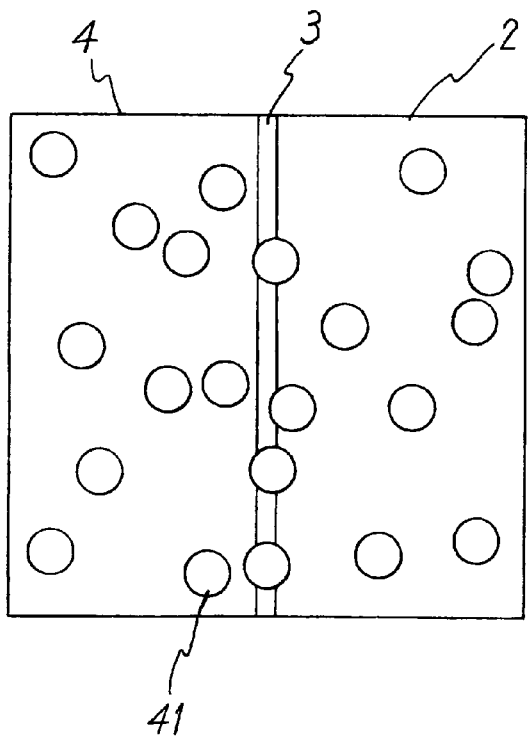
FIG. 4B shows a case in which the thickness of the core layer is thinner than the particle size of the deposited particles.

Next, sensors for measuring the deposit point having waveguide layers of three types of core layers having thicknesses of 6 $\mu$m, 200 $\mu$m, and 1 mm respectively were produced respectively to investigate the relationship between the thickness of the core layer 3 and the detection sensitivity. FIG. 4 conceptually shows magnified cross sections in the vicinity of the core layer 3 of the waveguide layer shown in FIG. 1 and relationships with respect to deposited particles 41. FIG. 4A shows a case in which the thickness of the core layer 3 is sufficiently thicker than the particle size of the deposited particles 41 such as those of paraffin wax. On the contrary, FIG. 4B shows a case in which the thickness of the core layer 3 is not larger than the particle size of the deposited particles 41. Initially deposited crystals can be highly sensitively detected by making the thickness of the core to be equivalent to or smaller than the deposited particles as shown in FIG. 4B. Accordingly, it has been found that the thinner thickness of the core layer is preferred. In the case of petroleum products, the particle size of deposited matters scarcely exceeds 1 mm. Therefore, the thickness of the core layer may be not more than 1 mm. It is desirable that the thickness of the core layer is not less than 1 $\mu$m in order to achieve waveguide for the light beam introduced into the core layer with little loss.

Method for measuring deposit point

The method for measuring the deposit point will be explained below, as exemplified by measurement of the cloud point of petroleum products. The cloud point of No. 2 gas oil was measured by using the total reflection type optical sensors including three types of waveguide layers having thicknesses of the core layer of 6 $\mu$m, 200 $\mu$m, and 1 mm respectively. The total reflection type optical sensor having the core thickness of the waveguide layer of 6 $\mu$m had the structure as shown in FIGS. 2 and 3.

On the other hand, each of the total reflection type optical sensors having the core thickness of the waveguide layer of 200 $\mu$m and 1 mm had a structure obtained by interposing each of waveguide glass plates (refractive index: 1.51) having the thicknesses of 200 $\mu$m and 1 mm between Pyrex glass plates (refractive index: 1.45) to make adhesion with an optical epoxy resin (refractive index: 1.45), and interposing an obtained assembly between Si substrates. An optical fiber array, in which a multiple mode optical fiber connected to a light emitting diode (LED) was embedded, was connected to a light-introducing surface. A photodetector (CCD sensor), which was connected to a computing unit for statistically processing the intensity of received light, was connected to a light-emitting surface (see FIG. 3).

At first, the sensor having the core thickness of 6 $\mu$m was used. With reference to FIG. 3, the central angle of incidence $\alpha$ was $\alpha=80°$, the spreading angle $\Delta$ was $\Delta$=about 4°, and the refractive index of the waveguide layer was 1.50. The light emitting diode (LED) for emitting a light beam having a central wavelength of 850 nm was used as a light source. The CCD sensor 32 was arranged to make it possible to detect the reflected light beam in an angle range of about 72° to about 88° of the spreading angle. Therefore, it was possible for the CCD sensor 32 to detect all reflected light beams having the spread angle range. In this system, No. 2 gas oil (refractive index $n_1$=about 1.48) had a critical angle of total reflection of about 80.5°. In general, when the method for measuring the cloud point is carried out, the refractive index of a deposit is larger than the refractive index of the test sample, and the refractive index of the deposit is often indefinite because the deposit is often a mixture. Therefore, it is practical to observe the change in reflected light intensity in the vicinity of the critical angle of total reflection of the test sample.

At first, the light intensity was measured by using the CCD sensor 32 while performing cooling to lower the temperature of No. 2 gas oil at a cooling speed of 0.1° C./second starting from room temperature by using a temperature control unit as described later on. A result is shown in a graph in FIG. 5. A range of 75° to 85° is indicated in the horizontal axis of the graph after converting, by calculation, the respective pixels of the CCD sensor 32 into the angle of emission. The vertical axis of the graph indicates the light intensity value. Light intensity values at respective temperatures are depicted as being consciously deviated so that the change in light intensity may be easily understood. Actual light intensity values at the respective temperatures are approximately coincident with each other in the vicinity of a range of angle of emission of 75° to 77°. A range of temperature of 1.5° C. to 0.1° C. is depicted in the graph. According to FIG. 5, it is understood that the critical angle of total reflection of No. 2 gas oil is 80.5°, and the light beam is transmitted at an angle not more than 80.5°. It is understood that when the temperature is lowered, the waveform of the peak is suddenly disturbed in the vicinity of 0.8° C. It is assumed that the disturbance is caused by the change in intensity of totally reflected light from No. 2 gas oil, as a result of deposition of paraffin component on the detecting surface from No. 2 gas oil. Namely, the cloud point of No. 2 gas oil was successfully measured within 10 minutes according to the change in intensity of totally reflected light.

In order to more accurately determine the cloud point according to the result shown in FIG. 5, light intensity data for the respective pixels of the CCD sensor 32 were statistically processed by using the following two methods. In the first method, the correlation coefficient between light intensity distributions obtained for every 0.1° C. was calculated as shown in the following expression (1) to investigate the relationship between the correlation coefficient and the temperature. In the expression (1), xi indicates light intensity detected by the pixel i at T °C., and yi indicates light intensity detected by the pixel i at T+0.1° C. Further, $\mu x$ and $\mu y$ indicates average values of the light intensities xi and yi of all of sampled pixels i, and $\sigma x$ and $\sigma y$ indicate standard deviations respectively. As for the judgment standard for determining the cloud point, the cloud point may be regarded to be a temperature at which the correlation coefficient $\rho xy$ is not more than a certain constant. In this embodiment, for example, the constant was designated as a numerical value obtained by subtracting a three-fold value of the standard deviation from the average of correlation coefficients between light intensity distributions at temperatures at which no deposit was found.

Correlation coefficient:

$$\rho_{xy} = \frac{\frac{1}{n}\sum_{i=1}^{n}(x_i - \mu_x)(y_i - \mu_y)}{\sigma_x \times \sigma_y} \quad (1)$$

Alternatively, another statistical processing method was used in order to accurately determine the cloud point according to the result shown in the graph in FIG. 5. Namely, the integral square A of differences between light intensity distributions obtained for every 0.1° C. was calculated in accordance with the following expression (2). In the expression, xi indicates the light intensity detected by the pixel i at T °C., and yi indicates the light intensity detected by the pixel i at T+0.1° C.

$$A = \sum_{i=1}^{n}(x_i - y_i)^2 \quad (2)$$

FIG. 6 shows the relationship between the temperature and the correlation coefficient calculated in accordance with the expression (1). Results are shown for a case in which the correlation coefficient was determined by substitutively using light intensity values obtained from the sensor array corresponding to the critical angle of total reflection of 80.5°±3° of No. 2 gas oil, and for a case in which the correlation coefficient was determined by using only light intensity values obtained from the sensor array corresponding to the critical angle of total reflection of 80.5°±1° of No. 2 gas oil respectively. According to FIG. 6, it is understood that the correlation coefficient is apparently lowered due to deposition at a temperature not more than 0.9°. It is understood that the change in correlation coefficient is drastic in the case of the critical angle of total reflection of 80.5°±1° in which the calculation range for the correlation coefficient is narrow. The cloud point can be sufficiently judged in the both cases in which the calculation range for the correlation coefficient corresponds to the critical angles of total reflection of 80.5°±1° and 80.5°±3°.

Figure 7:
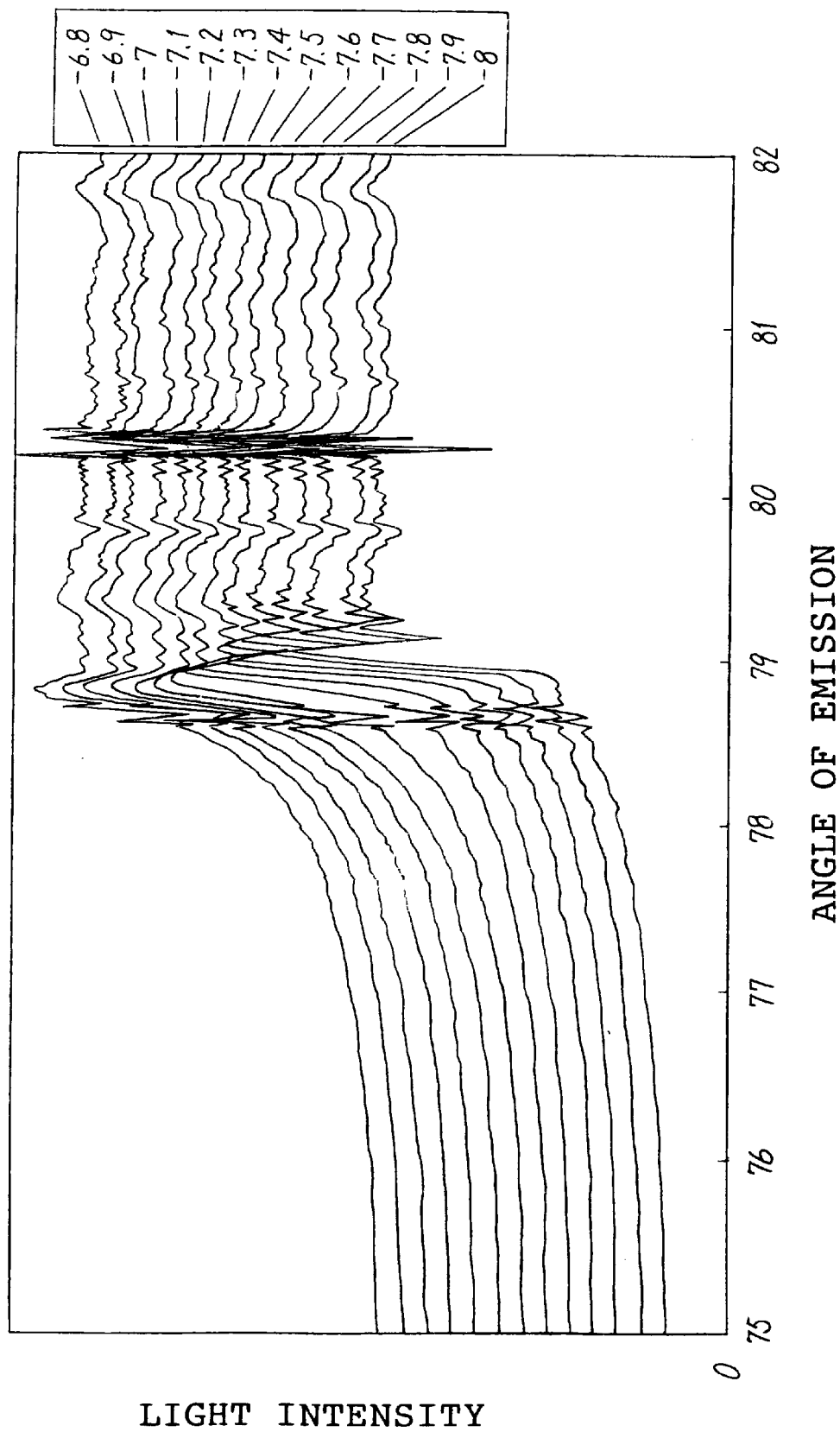
FIG. 7 shows a graph illustrating relationships between the angle of emission and the light intensity detected by the CCD sensor for No. 2 gas oil by using the sensor of the waveguide structure having a core thickness of 200 μm.

In FIG. 7, the cloud point was measured in the same manner as described above for No. 2 gas oil having a composition different from that used above, by using the sensor having the core thickness of 200 $\mu$m of the waveguide layer structure. The central angle of incidence $\alpha$ was $\alpha$=80°, the spreading angle $\Delta$ was $\Delta$=4°, and the refractive index of the waveguide layer was 1.5. However, the measurement was started at room temperature. Only light intensities, which correspond to temperatures in a range of −6.8° C. to −8° C. and angles of emission in a range of 75° to 82°, are shown in FIG. 7. In this system, the critical angle of total reflection of No. 2 gas oil is 78.7°. When comparison is made with FIG. 5, the change in intensity of the outgoing light beam, which was obtained when the temperature was progressively lowered, is extremely small. The change is merely in a degree in which small disturbance is observed in the vicinity of 79° at a temperature of not more than −7.5° C.

Figure 8:
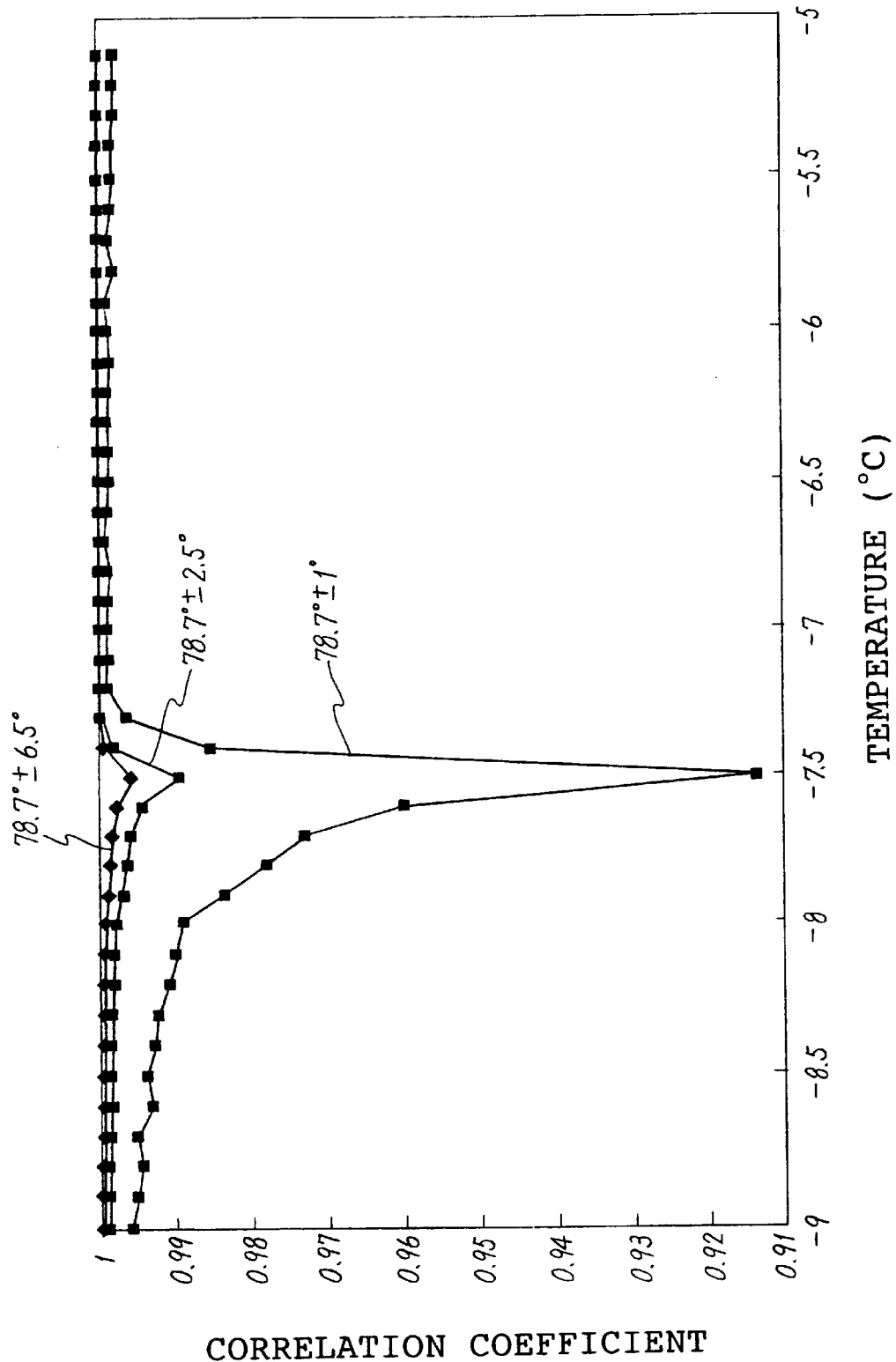
FIG. 8 shows a graph illustrating relationships between the correlation coefficient and the temperature obtained from the result shown in FIG. 7, depicting three cases based on the use of detection data from the sensor array corresponding to a critical angle of total reflection of 78.7°±6.5°, a critical angle of total reflection of 78.70°±2.5°, and a critical angle of total reflection of 78.7°±1° of No. 2 gas oil respectively.

FIG. 8 shows results obtained by using the results shown in FIG. 7 to calculate the correlation coefficient $\rho xy$ in accordance with the expression (1) for a case in which only light intensity values obtained from the sensor array corresponding to the critical angle of total reflection of 78.7°±6.5° of No. 2 gas oil were used, for a case in which only light intensity values obtained from the sensor array corresponding to the critical angle of total reflection of 78.7°±2.5° of No. 2 gas oil were used, and for a case in which only light intensity values obtained from the sensor array corresponding to the critical angle of total reflection of 78.7°±1° of No. 2 gas oil were used respectively. According to FIG. 8, the decrease in correlation coefficient was observed due to deposition at a temperature of not more than −7.5° C. when the temperature was progressively lowered, in the case of the use of the light intensity values obtained from the sensor array corresponding to the critical angle of total reflection of 78.7°±6.5°, and in the case of the use of the light intensity values obtained from the sensor array corresponding to the critical angle of total reflection of 78.7°±2.5°. Accordingly, it is understood that the cloud point can be judged in these cases. The correlation constant is approximately 1 which is constant at a temperature of not less than −7.0° C. The decrease in correlation coefficient was observed due to deposition at temperature of not more than −7.4° C. in the case of the use of the light intensity values obtained from the sensor array corresponding to the critical angle of total reflection of 78.7°±1°. Accordingly, the cloud point can be judged in this case.

Figure 9:
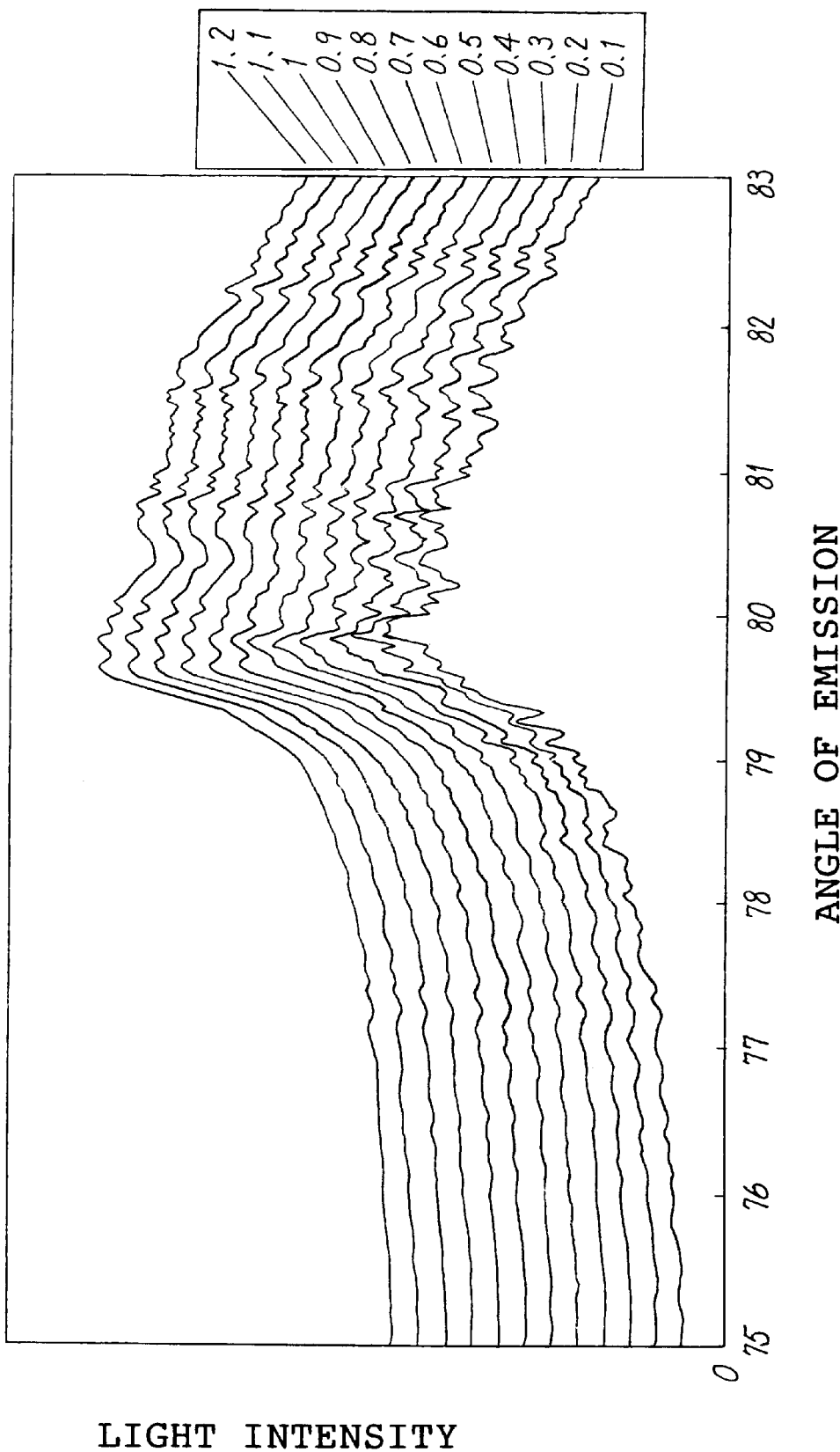
FIG. 9 shows a graph illustrating relationships between the angle of emission and the light intensity detected by the CCD sensor for No. 2 gas oil by using the sensor of the waveguide structure having a core thickness of 1 mm.

In FIG. 9, the cloud point was measured in the same manner as described above for No. 2 gas oil, by using the sensor having the core thickness of 1 mm of the waveguide layer structure. The central angle of incidence α was α=80°, the spreading angle Δ was Δ=4°, and the refractive index of the waveguide layer was 1.50. However, the measurement was started at room temperature. Only light intensities corresponding to temperatures in a range of 1.2° C. to 0.1° C. and angles of emission in a range of 75° to 83° are shown in FIG. 9. In this system, the critical angle of total reflection of No. 2 gas oil is 79.7°. When comparison is made with FIG. 5 in the same manner as described with reference to FIG. 7, the change in intensity of the outgoing light beam, which was obtained when the temperature was progressively lowered, is extremely small. The change is merely in a degree in which small disturbance is observed in the vicinity of 80° at a temperature of not more than −0.8° C.

Figure 10:
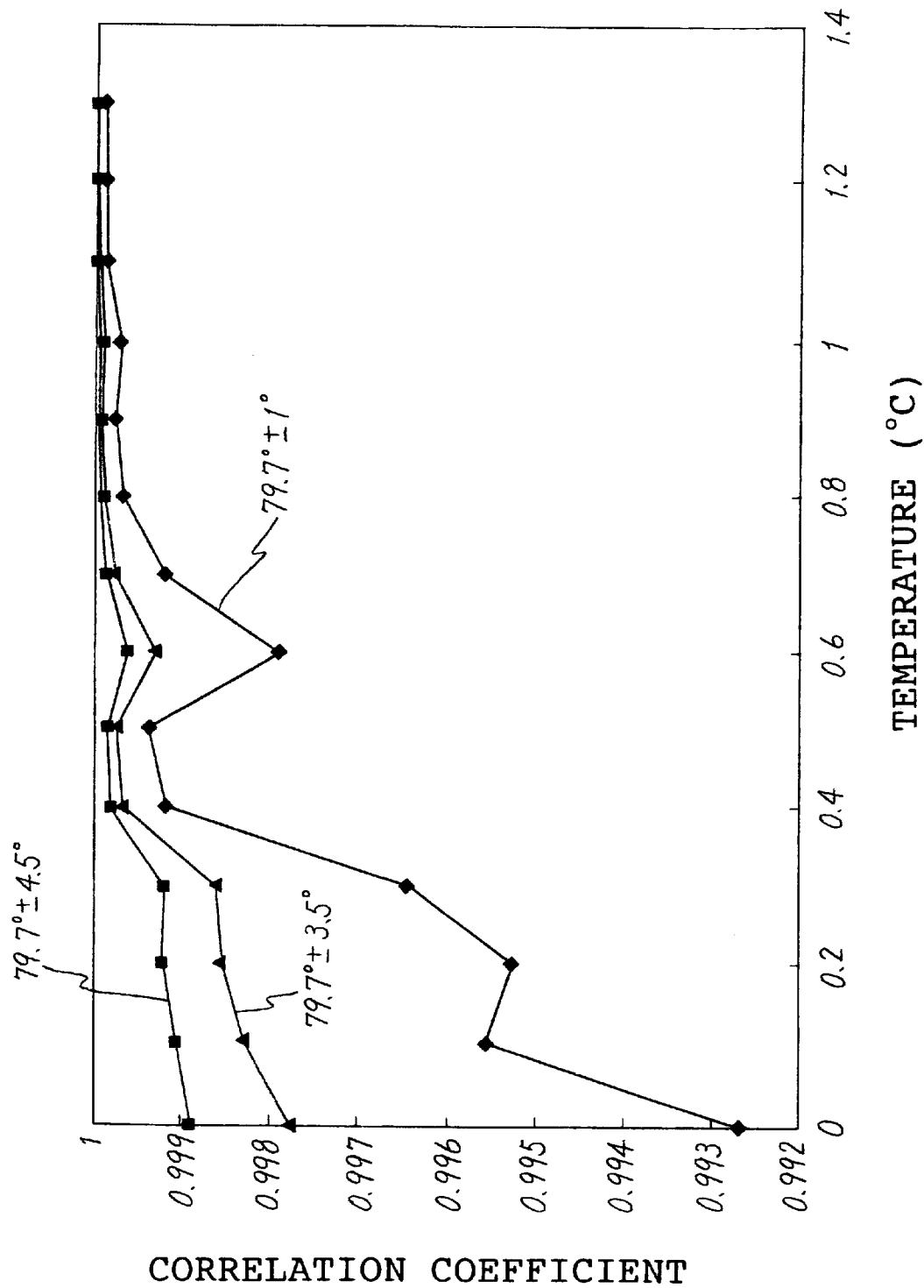
FIG. 10 shows a graph illustrating relationships between the correlation coefficient and the temperature obtained from the result shown in FIG. 9, depicting three cases based on the use of detection data from the sensor array corresponding to a critical angle of total reflection of 79.7°±4.5°, a critical angle of total reflection of 79.7°±3.5°, and a critical angle of total reflection of 79.7°±1° of No. 2 gas oil respectively.

FIG. 10 shows results obtained by using the results shown in FIG. 9 to calculate the correlation coefficient ρxy in accordance with the expression (1) for a case in which only light intensity values obtained from the sensor array corresponding to the critical angle of total reflection of 79.7°±4.5° of No. 2 gas oil were used, for a case in which only light intensity values obtained from the sensor array corresponding to the critical angle of total reflection of 79.7°±3.5° of No. 2 gas oil were used, and for a case in which only light intensity values obtained from the sensor array corresponding to the critical angle of total reflection of 79.7°±1° of No. 2 gas oil were used respectively.

The change in correlation coefficient was smaller by one digit than those obtained for the thicknesses of 6 μm and 200 μm of the core layer of the waveguide layer, even when the range of the light intensity value to be used for the calculation of the correlation coefficient was narrowed. The decrease in correlation coefficient was observed for all of the cases due to the deposition, from a temperature of not more than 1.1° C. However, the change is not so rapid as compared with those obtained when the thickness of the core layer of the waveguide layer was 6 μm and 200 μm. It is understood that the sensitivity is lowered when the thickness of the core layer is thick. In general, it is sufficient that the thickness of the core layer is not more than 1 mm.

Figure 11:
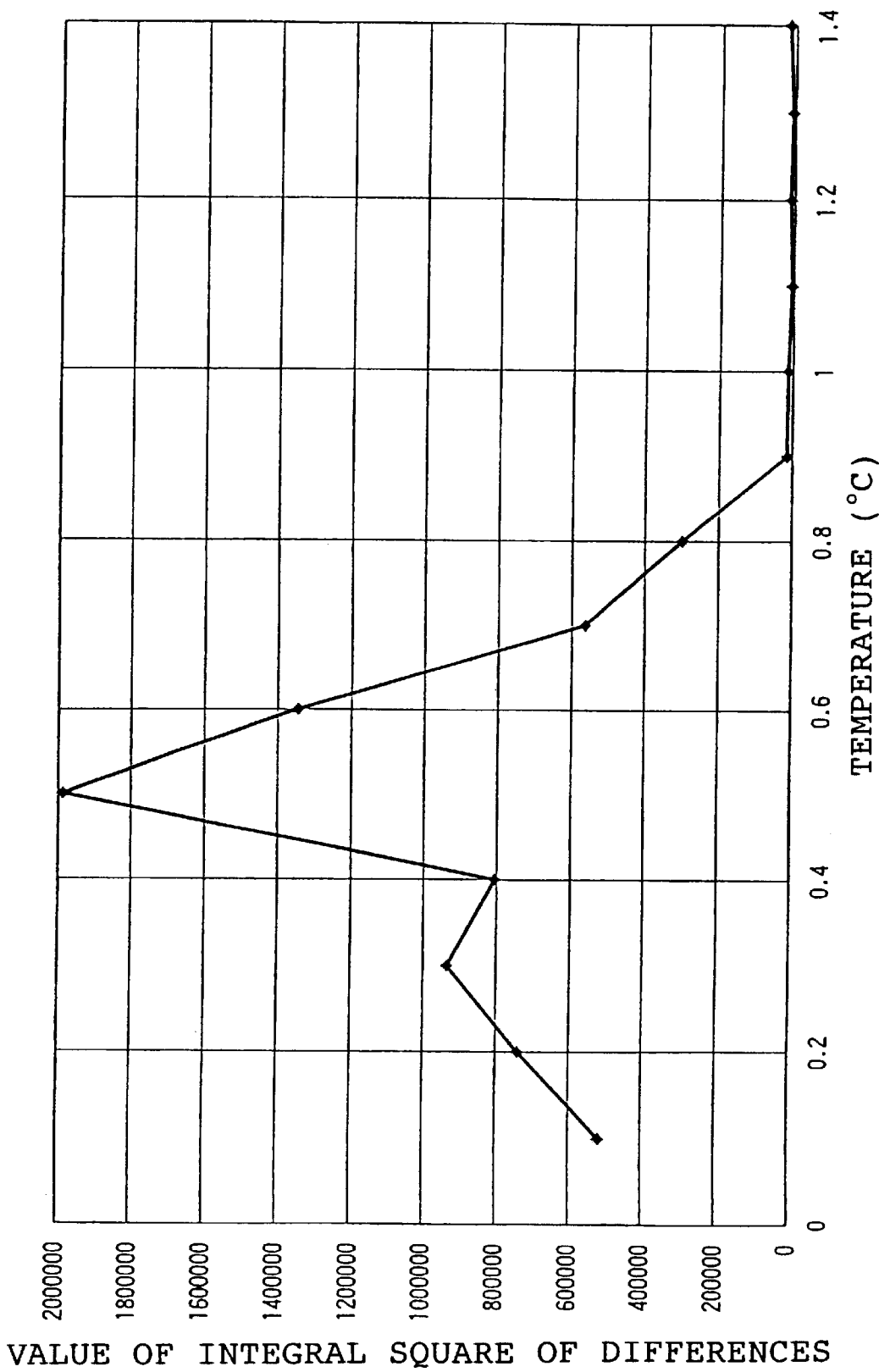
FIG. 11 shows a graph illustrating a result of calculation of integral square A of differences between light intensity distributions for every 0.1° C. according to the result shown in FIG. 5.

Next, the integral square A of differences between light intensity distributions of every 0.1° C. was calculated for the cooling temperature of every 0.1° C., from the result shown in FIG. 5 (core thickness: 6 μm) by using the expression (2) described above. The change in integral square A with respect to the respective temperatures is shown in a graph in FIG. 11. According to FIG. 11, it is understood that when the temperature is progressively lowered, the integral square A is suddenly increased in the vicinity of 0.9° C., making it possible to judge the cloud point.

The integral square A of differences between light intensity distributions for every 0.1° C. was calculated in the same manner as described above by using the expression (2), for the results of measurement for the light intensity with respect to the cooling temperature based on the use of the sensor of the waveguide structure having the core thickness of 200 μm and 1 mm (FIGS. 7 and 9). However, the integral square A greatly varied, and it was impossible to find any definite change from which the cloud point could be judged, probably because of the following reason. Namely, the measurement procedure may be affected by dispersion or irregularity in sensitivity of the CCD sensor or the like due to variation in temperature. In other words, such overall dispersion can be canceled in the case of the processing based on the expression (1), however, such overall dispersion cannot be canceled in the case of the processing based on the expression (2).

According to the methods described above, it took only about 10 minutes to perform the step for measuring the light intensity while cooling No. 2 gas oil as the test sample, and perform the statistical processing for determining the cloud point. Accordingly, it is understood that the measurement time is shortened as compared with the conventional method for measuring the cloud point. The cloud point was successfully measured at an accuracy of 0.1° C. The cloud point determined in accordance with the method of the present invention described above is certainly correlated with the cloud point of the same No. 2 gas oil measured by using the method for measuring the cloud point as specified in JIS K 2269. Thus, it has been found that the method of the present invention is a measuring method which is compatible with JIS K 2269.

Explanation has been made in the foregoing embodiments for the method for measuring the cloud point as the method for measuring the deposit point. However, the present invention is not limited to only the measurement for the cloud point. The present invention makes it possible to measure the dew point which exhibits the temperature at which water is deposited from vapor in gas, and measure the phase change associated with deposition such as those occur between liquid and solid, between gas and liquid, and between gas and solid. In the method for measuring the deposit point according to the present invention, the change in incoming light beam based on transmittance through a test sample is not measured, but the change in light reflection effected by a test sample is measured. Accordingly, it is possible to accurately measure the phase change of colored test samples, especially, it is possible to accurately measure the cloud point of petroleum products.

Assembly of deposit point meter

Figure 12A:
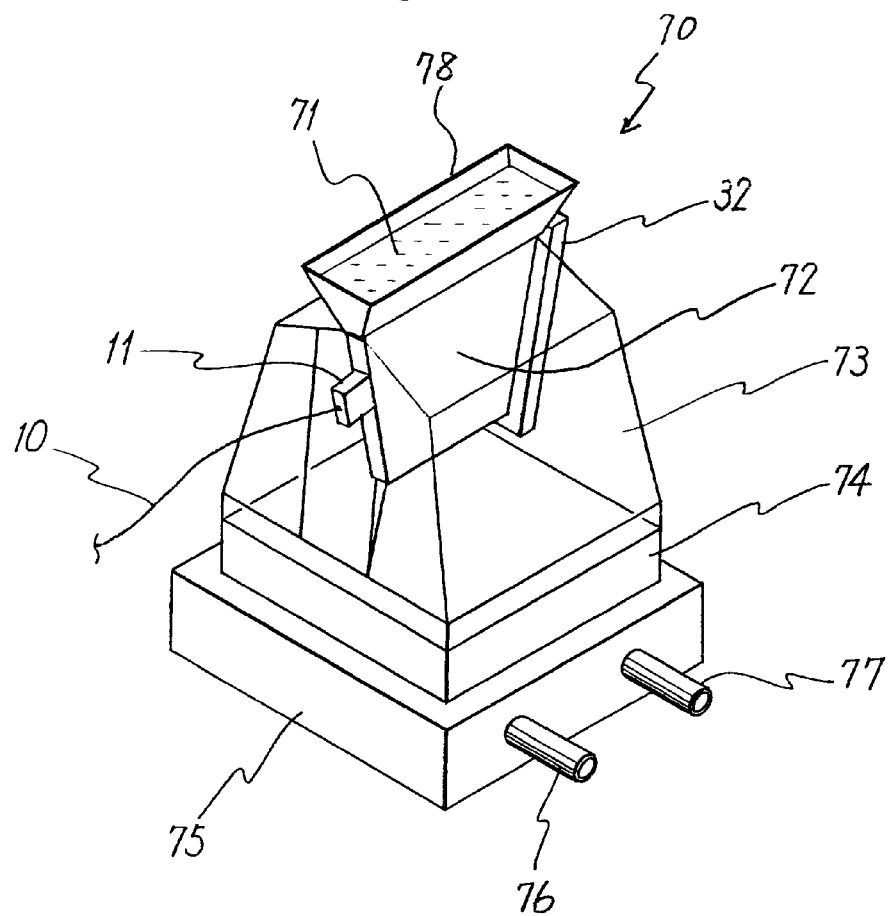
FIG. 12 shows a perspective view (FIG. 12A) and a side view (FIG. 12B) illustrating an example of the structure of the deposit point meter.
Figure 12B:
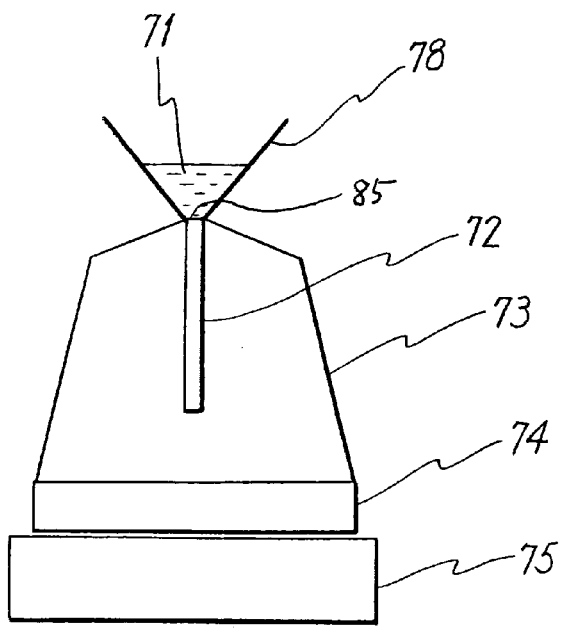

An example of the structure of the deposit point meter assembled by using the total reflection type sensor shown in FIGS. 2 and 3 is shown in a perspective view in FIG. 12A and in a side view in FIG. 12B. A cloud point meter 70 principally comprises a total reflection type sensor 72 installed with a CCD sensor 32 and a fiber 10 for supplying an incoming light beam, a hopper 78 for charging a test sample 71 therein, a Peltier element 74 for cooling the sensor 72 and the test sample 71, a thermal conductor (heat sink) 73 for surrounding the total reflection type sensor 72, and a temperature-measuring means (see FIG. 13) for measuring the temperature of a sensor head (detecting surface) 85. In the deposit point meter according to the present invention, the hopper 78 is installed on the sensor head 85 so that the sensor head 85 constitutes the bottom surface of the hopper 78. The test sample 71 is cooled via the sensor head 85. In the present invention, the deposit point is determined in accordance with the characteristics of reflected light from the deposit or depositing material deposited on the sensor head 85. Therefore, it is preferable that the temperature of the test sample is controlled via the detecting surface. By adopting the structure as described above, the deposit material is accumulated on the detecting surface, and the sensitivity to deposition is improved. Further, it is assumed that the test sample in the vicinity of the detecting surface has the same temperature as that of the detecting surface. Accordingly, this structure is advantageous in that the deposition temperature can be accurately monitored by measuring the temperature of the sensor head. The sensor 72 is embedded in the thermal conductor 73 as a heat sink installed on the Peltier element 74. Therefore, it is possible to control the heat uniformly and quickly. The cooling (temperature control) means for the sensor is not limited to the Peltier element. Alternatively, it is possible to use, for example, a heat exchanger based on the use of circulating coolant or refrigerant and a cryostat. As shown in the drawings, it is possible to install the Peltier element 74 on a water-cooling jacket 75 provided with an inlet 76 and an outlet 77 for cooling water.

Figure 13:
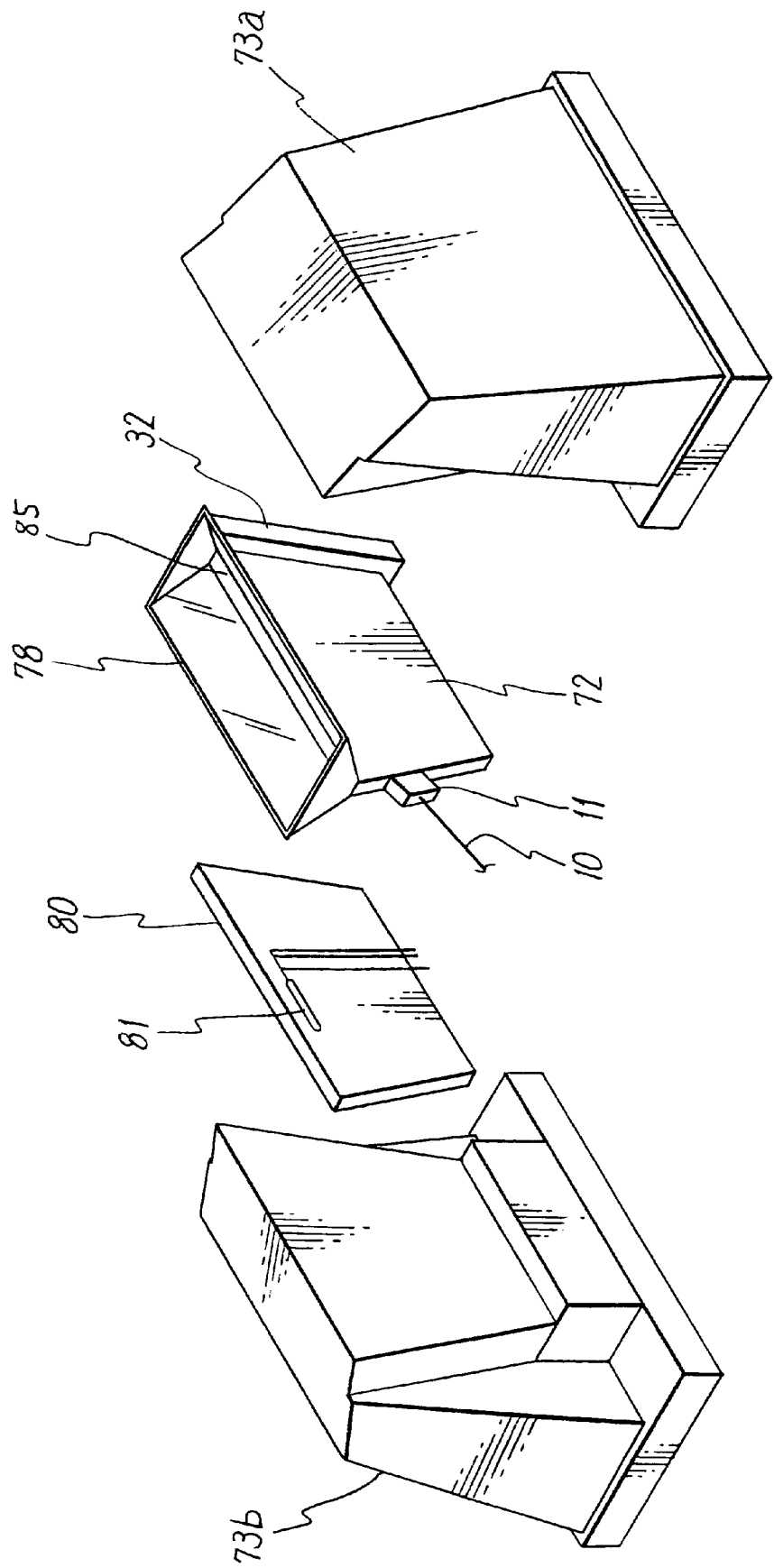
FIG. 13 shows an exploded perspective view of the assembly of a sensor portion of the deposit point meter shown in FIG. 12.

FIG. 13 shows an exploded perspective view of the assembly of the sensor portion of the cloud point meter 70 shown in FIG. 12. A silicon plate, which is affixed with a Pt resistance thermometer bulb (100 ohms) 81 as a temperature-detecting means, is joined to a side surface of the sensor 72. The Pt resistance thermometer bulb 81 is connected to a temperature control unit (not shown) for accurately controlling the temperature of the sensor head 85. The Peltier element 74 shown in FIG. 12 is subjected to temperature control by the aid of the temperature control unit. As shown in FIG. 13, the thermal conductor 73 as the heat sink is constructed by two members 73a, 73b, and the sensor 72 and the silicon plate 80 are interposed therebetween. Thus, it is possible to easily assemble the deposit point meter.

The method for measuring the deposit point and the deposit point meter according to the present invention have been specifically explained with reference to the embodiments. However, the present invention is not limited thereto, to which various alternations and improvements may be applied. For example, a plurality of optical fibers may be connected to the light-introducing optical path in order to widen the measurable range of the critical angle of total reflection. Further, a waveguide layer lens may be arranged at the connecting section between the waveguide assembly and the optical fiber in order to enlarge the spreading angle of the optical fiber. Alternatively, the detecting surface may be processed to have a concave configuration. Moreover, the light-emitting surface of the optical fiber may be processed to enlarge the spreading angle. When a plurality of optical fibers or light emitting elements are used to increase the angle of light incidence, it is preferable to make arrangement so that optical axes of the respective fibers or the like intersect with each other at one point on the detecting surface. In another viewpoint, it is easy to provide explosion proof by making connection via a tape fiber or the like, instead of direct connection of the light-emitting surface to the CCD sensor.

INDUSTRIAL APPLICABILITY

According to the method for measuring the deposit point of the present invention, the cloud point can be measured more accurately and more rapidly by detecting the light beam at the angle of incidence and the angle of reflection $\theta$ which satisfy $(\theta_1-\Delta)<\theta<(\theta_2+\Delta)$ provided that the incoming light beam has the spreading angle $\pm\Delta$, $\theta_1$ represents the critical angle of total reflection of the test sample, and $\theta_2$ represents the critical angle of total reflection of the deposit material deposited when the test sample is cooled. Further, when the deposit point meter of the present invention is used, the temperature, at which crystals of deposit material begin to be generated, can be accurately detected, because the test sample is cooled from the side of the detecting surface of the sensor. The thickness of the waveguide layer for constructing the sensor of the deposit point meter is not more than the size of particles deposited as a result of cooling for the test sample. Accordingly, the detection sensitivity of the sensor of the deposit point meter is extremely high. Therefore, the method for measuring the deposit point and the deposit point meter according to the present invention are extremely effective to quickly and highly accurately measure the cloud point of petroleum products such as gas oil.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for measuring a deposit point, comprising the steps of irradiating a test sample, for which the deposit point is measured, with a light beam from the outside and detecting a reflected light beam coming from a contact surface between the test sample and the outside, while changing a temperature of the test sample, characterized by:

irradiating the test sample with an incoming light beam at an angle of incidence $\theta$ which satisfies an expression $(\theta_1-\Delta)<\theta<(\theta_2+\Delta)$ while changing the temperature of the test sample, wherein the incoming light beam is a light beam having a spreading angle $\pm\Delta$, $\theta_1$ represents a critical angle of total reflection of the test sample, and $\theta_2$ represents a critical angle of total reflection of a deposit deposited when the test sample is cooled;

detecting a totally reflected light beam from the test sample;

and determining the deposit point of the test sample from a change in intensity of the totally reflected light beam with respect to the change in temperature, wherein a correlation coefficient between light intensity distributions of detected totally reflected light beams is determined as a function of temperature, and the deposit point is determined according to temperature-dependent change in the correlation coefficient.

2. The method for measuring the deposit point according to claim 1, wherein the deposit point is a cloud point.

3. The method for measuring the deposit point according to claim 1, wherein the sample is a petroleum product.

4. A deposit point meter comprising a sensor including a waveguide layer formed with a light-introducing optical path for introducing an incoming light beam onto a contact surface with respect to a test sample for which a deposit point is measured and a light-emitting optical path for emitting a reflected light beam coming from the contact surface, a light-supplying means connected to the waveguide layer for supplying the incoming light beam to the light-introducing optical path, and a photodetector connected to the waveguide layer for detecting the reflected light beam coming from the light-emitting optical path; and a heating and cooling means for controlling a temperature of the test sample; wherein:

the light-introducing optical path and the light-emitting optical path are formed in the waveguide layer so as to pass the incoming light beam and reflected light beam, respectively, when the incoming light beam has an angle of incidence $\theta$ with the contact surface, which satisfies an expression $(\theta_1-\Delta)<\theta<(\theta_2+\Delta)$, provided that the incoming light beam has a spreading angle $\pm\Delta$, $\theta_1$ represents a critical angle of total reflection of the test sample and $\theta_2$ represents a critical angle of total reflection of a deposit deposited when the test sample is cooled below a deposit point temperature and further comprising:

a computing unit for statistically processing intensities of light received by the photodetector, wherein the computing unit determines a correlation coefficient between light intensity distributions of totally reflected light beams detected by the photodetector, as a function of temperature, and the computing unit determines the deposit point according to temperature-dependent change in the correlation coefficient.

5. The deposit point meter according to claim 4, wherein the waveguide layer is a core and is a part of a laminate having a clad/core/clad-configured structure on a substrate, the light supplying means includes an optical fiber for supplying the incoming light beam to the light-introducing optical path, and the photodetector includes a photoelectric sensor array for detecting the reflected light beam coming from the light-emitting optical path, and wherein the laminate includes a light-introducing surface connected to the optical fiber, the contact surface for totally reflecting or transmitting the incoming light beam, and a light-emitting surface connected to the photoelectric sensor array.

6. The deposit point meter according to claim 5, wherein a material of the core/clad is selected from the group consisting of $SiO_2/SiO_2+GeO_2$, $SiO_2/SiO_2+TiO_2$, and $SiO_2+SiF_4/SiO_2$.

7. The deposit point meter according to claim 5, wherein the core has a thickness which is not more than 1 mm.

8. The deposit point meter according to claim 4, wherein the test sample is cooled on a side of the contact surface of the sensor.

9. The deposit point meter according to claim 4, further comprising a hopper for containing the test sample therein, wherein the contact surface forms a bottom surface of the hopper.

10. A method for measuring a deposit point, comprising the steps of irradiating a test sample, for which the deposit point is measured, with a light beam from the outside and detecting a reflected light beam coming from a contact surface between the test sample and the outside, while changing a temperature of the test sample, characterized by:

irradiating the test sample with an incoming light beam at an angle of incidence $\theta$ which satisfies an expression $(\theta_1-\Delta)<\theta<(\theta_2+\Delta)$ while changing the temperature of the test sample, wherein the incoming light beam is a light beam having a spreading angle $\pm\Delta$, $\theta_1$ represents a critical angle of total reflection of the test sample, and $\theta_2$ represents a critical angle of total reflection of a deposit deposited when the test sample is cooled;

detecting a totally reflected light beam from the test sample;

and determining the deposit point of the test sample from a change in intensity of the totally reflected light beam with respect to the change in temperature, wherein an integral square of differences between light intensity distributions of detected totally reflected light beams is determined as a function of temperature, and the deposit point is determined according to temperature-dependent change in the integral square.

11. The method for measuring the deposit point according to claim 10, wherein the deposit point is a cloud point.

12. The method for measuring the deposit point according to claim 10, wherein the sample is a petroleum product.

13. A deposit point meter comprising a sensor including a waveguide layer formed with a light-introducing optical path for introducing an incoming light beam onto a contact surface with respect to a test sample for which a deposit point is measured and a light-emitting optical path for emitting a reflected light beam coming from the contact surface, a light-supplying means connected to the waveguide layer for supplying the incoming light beam to the light-introducing optical path, and a photodetector connected to the waveguide layer for detecting the reflected light beam coming from the light-emitting optical path; and a heating and cooling means for controlling a temperature of the test sample; wherein:

the light-introducing optical path and the light-emitting optical path are formed in the waveguide layer so as to pass the incoming light beam and reflected light beam, respectively, when the incoming light beam has an angle of incidence $\theta$ with the contact surface, which satisfies an expression $(\theta_1-\Delta)<\theta<(\theta_2+\Delta)$, provided that the incoming light beam has a spreading angle $\pm\Delta$, $\theta_1$ represents a critical angle of total reflection of the test sample and $\theta_2$ represents a critical angle of total reflection of a deposit deposited when the test sample is cooled below a deposit point temperature and further comprising:

a computing unit for statistically processing intensities of light received by the photodetector, wherein the computing unit determines an integral square of differences between light intensity distributions of totally reflected light beams detected by the photodetector, as a function of temperature, and the computing unit determines the deposit point according to temperature-dependent change in the integral square.

14. The deposit point meter according to claim 13, wherein the waveguide layer is a core and is a part of a laminate having a clad/core/clad-configured structure on a substrate, the light supplying means includes an optical fiber for supplying the incoming light beam to the light-introducing optical path, and the photodetector includes a photoelectric sensor array for detecting the reflected light beam coming from the light-emitting optical path, and wherein the laminate includes a light-introducing surface connected to the optical fiber, the contact surface for totally reflecting or transmitting the incoming light beam, and a light-emitting surface connected to the photoelectric sensor array.

15. The deposit point meter according to claim 14, wherein a material of the core/clad is selected from the group consisting of $SiO_2/SiO_2+GeO_2$, $SiO_2/SiO_2+TiO_2$, and $SiO_2+SiF_4/SiO_2$.

16. The deposit point meter according to claim 14, wherein the core has a thickness that is not more than 1 mm.

17. The deposit point meter according to claim 13, wherein the test sample is cooled on a side of the contact surface of the sensor.

18. The deposit point meter according to claim 13, further comprising a hopper for containing the test sample therein, wherein the contact surface forms a bottom surface of the hopper.

* * * * *

UNITED STATES PATENT AND TRADEMARK OFFICE
CERTIFICATE OF CORRECTION

PATENT NO. : 6,076,959
DATED : June 20, 2000
INVENTOR(S) : Yasushi Nagasawa

It is certified that error appears in the above-identified patent and that said Letters Patent is hereby corrected as shown below:

Title page,
Item [86], please change the § 371 Date from "Mar. 3, 1998" to -- April 6, 1998 --; and please change the § 102(e) Date from "Mar. 3, 1998" to -- April 6, 1998 --.

Signed and Sealed this

Twenty-third Day of April, 2002

Attest:

JAMES E. ROGAN
Director of the United States Patent and Trademark Office

Attesting Officer